United States Patent [19]

Woods et al.

[11] Patent Number: 4,533,085

[45] Date of Patent: Aug. 6, 1985

[54] METHOD FOR PRODUCTION OF A SUSPENSION OF ZIRAM

[76] Inventors: Jay A. Woods; Verle W. Woods; Dale G. Woods, all of P.O. Box 1016, Yakima, Wash. 98907

[21] Appl. No.: 518,749

[22] Filed: Jul. 29, 1983

[51] Int. Cl.³ .............................................. B02C 19/12
[52] U.S. Cl. ........................................ 241/1; 71/111; 241/21; 241/23; 514/494
[58] Field of Search .................... 241/23, 1, 30, 21, 15, 241/16, 17, 22, 62; 71/111; 260/429.9; 252/306; 424/289, 353, 354, 168, 322, 352, 38

[56] References Cited

U.S. PATENT DOCUMENTS

| | | |
|---|---|---|
| 2,492,314 | 1/1945 | Olin et al. . |
| 2,957,803 | 10/1960 | Woods . |
| 3,184,380 | 5/1965 | Woods . |
| 3,539,115 | 11/1970 | Woods . |
| 3,960,333 | 6/1976 | Woods et al. . |

*Primary Examiner*—Mark Rosenbaum
*Attorney, Agent, or Firm*—Wells, St. John & Roberts

[57] ABSTRACT

A method for synthesizing Ziram in a flowable water based suspension by reacting chemical starting materials in liquid components required for a final stable suspension of the resulting pesticide. The method applies to production of Ziram suspensions for pesticidal applications.

2 Claims, No Drawings

METHOD FOR PRODUCTION OF A SUSPENSION OF ZIRAM

FIELD OF THE INVENTION

The present invention relates to a process of preparing suspensions of Ziram.

BACKGROUND OF THE INVENTION

In U.S. Pat. No. 2,957,803, granted Oct. 25, 1960 and titled "Method of Preparing Suspension of Insecticides", is disclosed a method of forming a stable suspension of water insoluble organic pesticides comprising the steps of forming a liquid emulsion of fat or oil in water made heavier by a substance soluble in the water, introducing the solids into the liquid emulsion, to particles of a fineness of the order of 5 to 15 microns while agitating the liquid and solids together.

In U.S. Pat. No. 3,184,380, granted May 18, 1965 and titled "Stabilization of Concentrated Suspensions of Pesticide Particles", is disclosed a method of improving the uniformity of such a suspension when the chemicals being suspended have certain characteristics. It applies to certain water insoluble pesticide chemicals having a crystalline form in the range of temperatures at which they are stored and used. They also (1) must have a melting point below its decomposition temperature and below the boiling point of the suspending solution, or (2) be substantially totally soluble in the coating fat below the boiling point of the suspending liquid and below its decomposition temperature. A suspension made according to U.S. Pat. No. 2,957,803 can then be heated until melting occurs. After cooling the resulting suspension has a much finer and/or uniform particle size.

We have discovered that we are now able to improve the uniformity of the suspension for an additional pesticide. The present method is directed to the synthesis of Ziram, which has utility as a pesticide when applied to growing crops by spraying in a suspension.

U.S. Pat. No. 2,492,314 discloses a direct reaction method for synthesizing insoluble metal salts of substituted dithiocarbamic acids, including Ziram. The chemical system used for synthesis is essentially dry, although some of the listed examples discuss the use of water for mixing purposes only. The resulting products are stated to be dry.

DESCRIPTION OF THE PREFERRED EMBODIMENT

In compliance with the constitutional purpose of the Patent Laws "to promote the progress of science and useful arts" (Article 1, Section 8), applicant submits the following disclosure of the invention.

The present disclosure is directed to the synthesis of Ziram, an organic pesticide having the following chemical name: zinc dimethyl dithiocarbamate.

A general discussion of the materials and steps involved in production of pesticide suspensions as utilized in the present method of can be found in the disclosures of U.S. Pat. Nos. 2,957,803 and 3,184,380, which are incorporated into this disclosure by reference.

This disclosure is directed to the synthesis of Ziram during production of a liquid suspension in water in a flowable form readily dispersible in greater volumes of water for field application purposes. The synthesized pesticide is an organic solid having very small particle size, typically less than 5 microns in average diameter.

To form the desired suspension, the pesticide particles are mixed as they are synthesized with a liquid base containing water emulsifiers, and a suitable fat or oil, the base will often require addition of a non-reactive water soluble substance that increases the specific gravity of the resultant liquid.

As used herein, the term "fat" shall include liquids commonly referred to as oils, as well as those substances commonly referred to as fats, regardless of whether they are of animal, vegetable or mineral origin. Suitable materials are lard, tallow, mineral oil, and margarine.

The specific gravity of the liquid can be increased by addition of any material soluble in water and having no appreciable reactive activity with respect to the fat or other suspension components. Examples are urea, sugar, molasses and sulfide waste liquor.

The suspension also includes a suitable emulsifying agent. This can be selected from the many commercial emulsifiers available for water-based suspensions.

For present purposes, the term "agitate" shall mean the vigorous stirring, mixing or moving of a suspension or mixture so as to continuously alter the relative positions of the particles within it. Such agitation is accomplished quite readily by flowing the mixture or suspension through a recirculating pump. Other equivalent agitation methods can be substituted. Agitation of the suspended materials as described herein can also include grinding or breaking of particles as they are mixed. This can be achieved by using pump impeller blades having impacting teeth formed thereon, as shown in U.S. Pat. No. 2,957,803, or by the use of fluidic mills capable of recirculating liquid components while pumping them or in conjunction with pumping action. Examples of such mills are disclosed in U.S. Pat. Nos. 3,539,115 and 3,960,333, which are incorporated into this disclosure by reference.

In general, this method involves agitating and reacting a mixture of starting materials for the pesticide in a water suspension, and subsequently adding any remaining constituents of fat, emulsifier and water to complete a stable flowable pesticidal formulation that can subsequently be readily dispersed in greater volumes of water following storage and transportation.

More specifically, the method requires continuously agitating an initial suspension of a first water-insoluble starting material, emulsifier and water. A second starting material is then thoroughly dispersed within the agitated initial suspension. Agitation of the suspension is continued while maintaining it at a preselected reactive temperature range over a time period sufficient to assure that reactions between the first and second starting materials are completed by production of the pesticide in the suspension. The proportion of liquid components in the suspension must be preselected so as to maintain the suspension in a fluid state suitable for agitation at all times. After completion of the reactions, the suspension might be completed by adding remaining non-reactive constituents to complete a stable flowable pesticidal suspension.

Further details of the general method will be evident from the specific example which follows.

An 1889 pound batch of Ziram (zinc dimethyl dithiocarbamate) was produced from the following list of ingredients:

241 lbs. water
180 lbs. urea
28 lbs. emulsifier (Sponto N-300B)

55 lbs. emulsifier (Sponto N-500B)
425 lbs. oil (Witco 9093)
380 lbs. carbon disulfide
205 lbs. zinc oxide
375 lbs. dimethyl amine (60%)

In the synthesis of Ziram, the first starting material is a mixture of finely divided zinc oxide and carbon disulfide. The second starting material for the reaction is finely divided dimethyl amine.

Ziram is synthesized by first forming a liquid suspension of the carbon disulfide, emulsifier and oil in water containing dissolved urea to modify the specific gravity of the water. The zinc oxide is then added to the suspension. Finally, the dimethyl amine is added to the suspension. The mixture must be continuously agitated. Its temperature should be maintained below 40° C. by cooling until the production of Ziram has been completed. The proportions of the liquid components in the reacting suspension were preselected to provide the desired end concentration of pesticide in a flowable liquid suspension at the expected reaction efficiency. The reaction efficiency for production of Ziram in the suspension is very close to theoretical. The ingredients listed above produce a resulting suspension containing 40% Ziram by weight.

While it is preferable to first dissolve the urea in the water, then add the emulsifiers and the oil, and finally add carbon disulfide in the initial agitated solution, the order of addition of these elements is not critical to the process. However, these elements should be thoroughly mixed and agitated prior to adding zinc oxide to produce a water-based suspension of zinc oxide. The dimethyl amine should then be added relatively slowly. This can be achieved by dropping it into the suspension behind an agitating pump so that it is dispersed during pumping and recycling of the suspension components. The temperature of the reacting suspension should be maintained below 40° C. by cooling, and must not be permitted to exceed 46° C., which is the boiling point of carbon disulfide.

The reaction to produce Ziram occurs within minutes after the addition of the dimethyl amine and rapidly proceeds to completion. The result is a flowable suspension of Ziram that is readily dispersible in greater volumes of water for field use. The Ziram is finely divided and the resulting suspension has an acceptable shelf life for storage purposes.

The above example is only illustrative of the application of this invention to the production of a pesticidal suspension of Ziram. The novelty in the process does not reside in the basic chemical reaction used to produce the pesticide (which is known) nor in the selection of suspension materials (which is described in U.S. Pat. Nos. 2,957,803 and 3,184,380). The novel aspect of this process is the successful synthesis of Ziram in a suspension, thereby eliminating the handling and expense of first synthesizing the chemical and subsequently producing a stable suspension.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. A method of synthesizing zinc dimethyl dithiocarbamate (Ziram) in a flowable water-based suspension, comprising the following steps:

continuously agitating an initial suspension containing a mixture of finely divided zinc oxide and carbon disulfide and liquid components including an emulsifier and water;

thoroughly dispersing finely divided dimethyl amine within the initial suspension;

continuing agitation of the suspension while maintaining it at a preselected reactive temperature range for a time period sufficient to assure that reactions between the mixture of finely divided zinc oxide and carbon disulfide and the finely divided dimethyl amine is completed by production of Ziram in the suspension;

the proportion of liquid components in the initial suspension being preselected so as to maintain the suspension in a fluid state suitable for agitation at all times while the reactions are occurring;

and subsequently mixing the suspension while adding fat, emulsifier or water as required to produce a stable flowable Ziram suspension.

2. A method of synthesizing zinc dimethyl dithiocarbamate (Ziram) as a flowable pesticidal suspension in water, comprising the following steps:

forming a liquid suspension of carbon disulfide, emulsifier and oil in water;

adding zinc oxide to the liquid suspension;

then adding dimethyl amine to the liquid suspension while continuously agitating it and maintaining its temperature below 40° C. until the production of Ziram has been completed within it;

the proportion of liquid components in the liquid suspension being preselected to provide the desired end concentration of Ziram in a flowable liquid suspension.

* * * * *